United States Patent [19]

Johnsen

[11] Patent Number: 4,616,912
[45] Date of Patent: Oct. 14, 1986

[54] APPARATUS FOR THE PHOTOGRAPHIC RECORDING OF PLATE THERMOGRAPHY

[75] Inventor: Andreas O. Johnsen, Griesheim, Fed. Rep. of Germany

[73] Assignee: Röhm GmbH, Darmstadt, Fed. Rep. of Germany

[21] Appl. No.: 650,088

[22] Filed: Sep. 13, 1984

[30] Foreign Application Priority Data

Sep. 14, 1983 [DE] Fed. Rep. of Germany ... 8326341[U]

[51] Int. Cl.⁴ .............................................. G03B 29/00
[52] U.S. Cl. ...................................... 354/80; 354/82
[58] Field of Search ..................... 354/80–82, 354/293; 355/21, 39

[56] References Cited

U.S. PATENT DOCUMENTS

| | | | |
|---|---|---|---|
| 2,667,825 | 2/1954 | Nicholas | 354/80 |
| 3,917,944 | 11/1975 | Eisenberger et al. | 354/424 X |
| 4,060,654 | 11/1977 | Quenneville | 428/1 |
| 4,079,529 | 3/1978 | Jennen et al. | 38/102.2 |
| 4,101,696 | 7/1978 | Jennen et al. | 428/1 |
| 4,185,904 | 1/1980 | Eddy | 354/80 |
| 4,217,373 | 8/1980 | Jennen et al. | 427/2 |
| 4,268,155 | 5/1981 | Lehnert et al. | 354/80 X |
| 4,301,054 | 11/1981 | Buirley et al. | 260/29.4 |
| 4,405,223 | 9/1983 | Shull | 354/82 X |

FOREIGN PATENT DOCUMENTS 687588 2/1953 United Kingdom ............... 354/293

Primary Examiner—L. T. Hix
Assistant Examiner—Brian W. Brown
Attorney, Agent, or Firm—Curtis, Morris & Safford

[57] ABSTRACT

A compact apparatus of light-weight construction for the performance and simultaneous photographic recording of plate thermography is disclosed which comprises two similar elongated parallely extending rails to whose rear ends there is mounted upright, at right angles to and interconnecting them, a frame for holding a thermographic plate. A camera mount is secured to the front ends of the rails and interconnects them. At least one crossbar is secured to the rails and carries at each end a flash unit. A camera operating grip is mounted obliquely at the approximate center of gravity of the compact apparatus by means of a mounting bar interconnecting the two rails. The grip is provided with electric cables for tripping the flash unit and the camera. The frame includes a plastic channel for the vertical mounting of the thermograph plate internally adjacent thereto, thereby to leave the thermographic plate substantially free. The frame also has magnetic adhesion means at least along its upper edge and binlike sections disposed between the frame and the crossbar or the mounting bar.

6 Claims, 2 Drawing Figures

APPARATUS FOR THE PHOTOGRAPHIC RECORDING OF PLATE THERMOGRAPHY

BACKGROUND OF INVENTION

The present invention relates to apparatus for the performance of liquid-crystal plate thermography with simultaneous photographic recording, and more particularly to such an apparatus which is compact in construction.

Pictorial representations of temperature distributions on objects can be obtained in a relatively simple known manner with the use of liquid crystals. One such technique is known as plate thermography, wherein thermographic plates are used that consist of a foil substrate coated with liquid crystals. When these thermographic plates are brought into contact with the skin, for example, the liquid crystals assume a color corresponding to the local heat content of the skin area.

Plate thermography has acquired special importance as a diagnostic aid. Since inflammatory and neoplastic changes influence the generation and transport of heat in tissue, these deviations from normal physiological processes result in recordable temperature differences at the skin surface.

One field of application for plate themography which has been attracting increasing attention recently is the diagnostic detection of breast cancer. Appropriate devices such as thermographic foils are on the market for use in this field. A particularly promising design of thermographic foil is the breast thermodetector. This is a flexible foil with two windows which permit the simultaneous plate-thermographic observation of both breasts in one step.

BRIEF DESCRIPTION OF THE INVENTION

The lack of adequate photographic recording facilities has militated against the wide spread use of plate thermography in breast examinations. What has been needed is an apparatus permitting photographs of the thermographic clinical picture of the breasts to be made under recording conditions which are as nearly constant and as favorable as possible. Moreover, to do this certain requirements would have to be met which it previously seemed could not readily be satisfied in a single apparatus. These requirements include, for example: (i) optimization of the optical arrangement of thermographic plate, camera and flash unit to yield reflection-free pictures; (ii) synchronization of a second flash unit; (iii) fixing of the thermographic plate without interfering with the reading of the thermogram; and (iv) adjustability of image area with respect to height.

In addition, the apparatus should make use, to the extent possible, of readily available components to permit it to be manufactured economically.

Accordingly it is an object of the present invention to provide a compact apparatus for the photographic recording of plate thermography.

Another object of the present invention is to fix a thermographic plate without interfering with the reading of the thermogram.

Yet another object of the invetion is to produce a reliable apparatus for the photographic recording of plate thermography using known components.

A further object of the invention is to provide apparatus for the photographic recording of plate thermography which is relatively simple in construction and easy to manufacture.

A still further object of the present invention is to provide apparatus for the photographic recording of plate thermography which is inexpensive to manufacture yet durable in use.

In accordance with an aspect of the present invention a compact apparatus for the photographic recording of plate thermography is provided which is of lightweight construction and formed of components which are already available. The apparatus includes a pair of elongated rails arranged side by side and preferably parallel to each other. A holding frame is mounted on the rear ends of these rails and at right angles to them. The frame interconnects the rails and serves to support a thermographic plate. A camera mount is secured to the front ends of the rails and also interconnects them. At least one crossbar is secured to the rails and carries at each of its ends a flash unit. A grip is mounted obliquely at the approximate center of gravity of the compact apparatus by means of a mounting bar interconnecting the two rails. The grip is provided with a release and electric cables for tripping the flash units and the camera.

The above, and other objects, features and advantages of the invention will be apparent in the following detailed description of an illustrative emobodiment thereof, wherein:

FIG. 1 is a side elevational view of the apparatus of the present invention; and FIG. 2 is a perspective view of the apparatus shown in FIG. 1.

DETAILED DESCRIPTION

Figure 1:
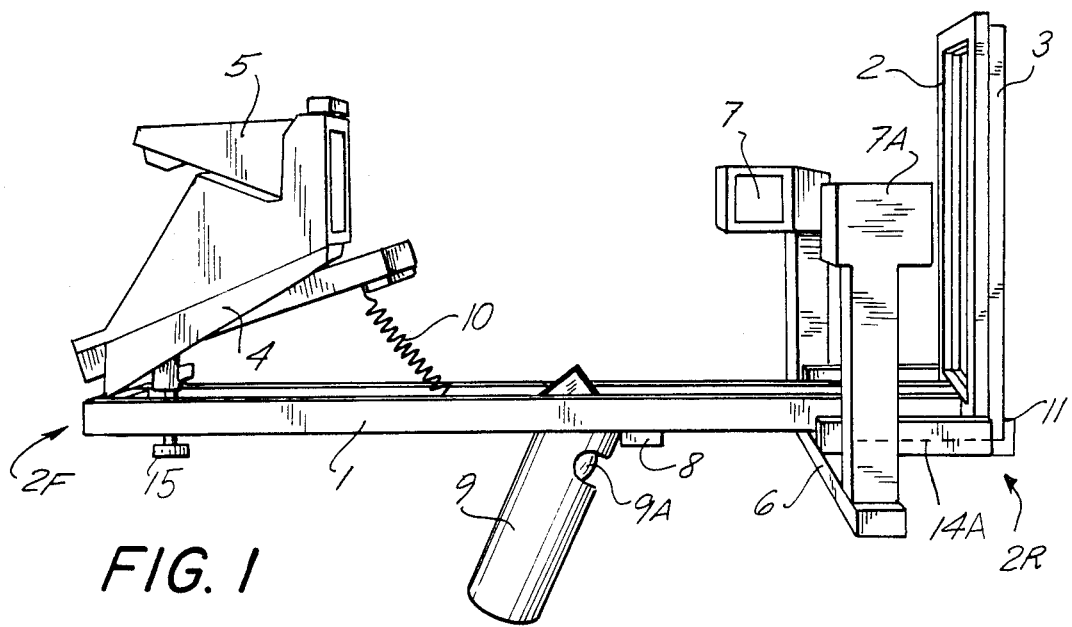

Referring now to the drawings in detail the apparatus of the invention includes a pair of elongated parallely extending main rails 1, 1A having opposed front and rear ends 2F, 2R respectively. A generally rectangular frame 2 is secured to the rear ends 2R of rails 1, 1A and interconnects therein. The frame, as described thereinafter serves to support a thermographic plate when the device is in use.

A front frame element 5A is connected in any convenient manner to the front ends 2F of rails 1, 1A and a camera mount 4 is mounted thereon. A camera 5 is seated in mount 4 in any known manner.

Figure 2:
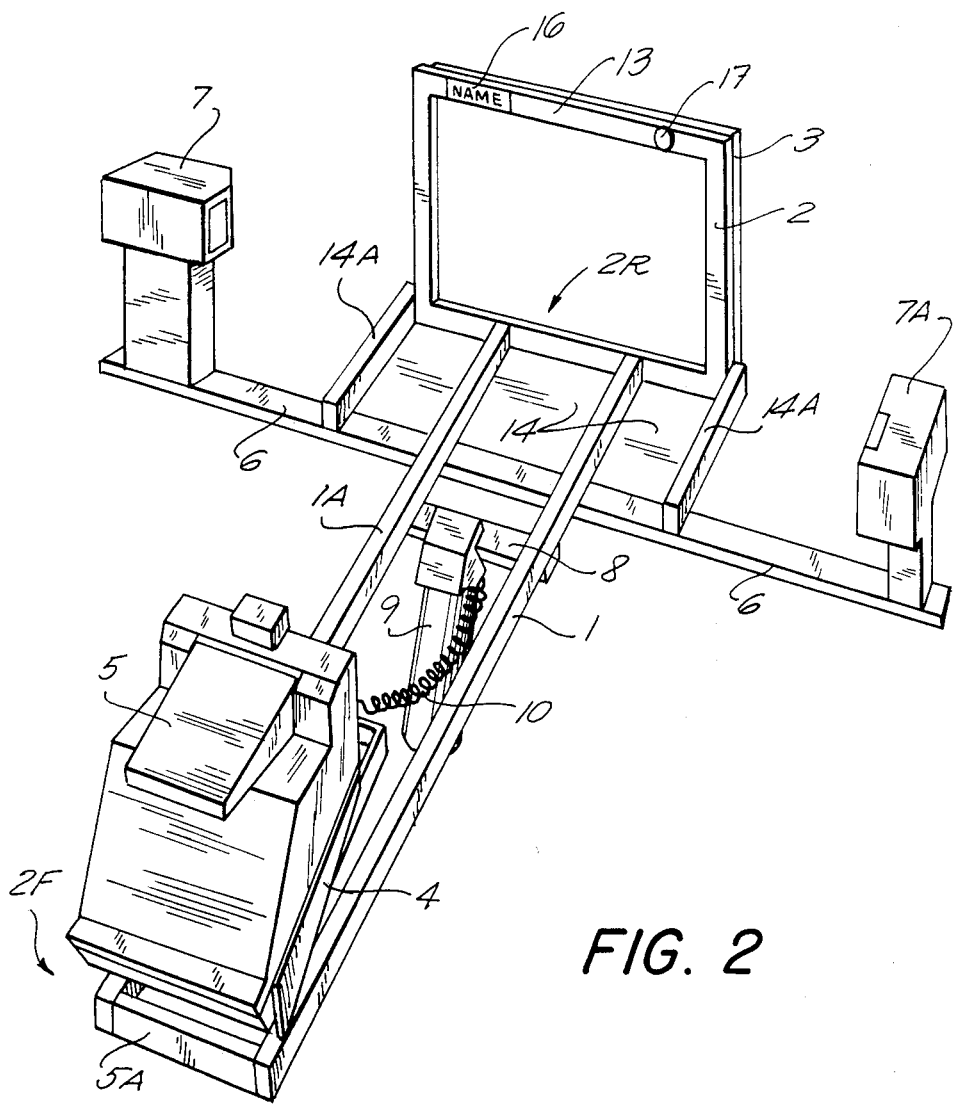

An elongated support bar 6 extends generally perpendicularly to and across rails 1, 1A. The support bar 6 is secured to the rails in any convenient manner. Conventional photographic flash units 7, 7A are mounted on the opposed free ends of cross bar 6, as seen in FIG. 2.

A second support bar 8 is mounted between rails 1, 1A at approximately the center of gravity of the unit. A camera operating grip 9 is mounted on bar 8 in any convenient manner. Thus the unit will be generally balanced when supported in the hand with grip 9. The grip is connected by conventional release and electrical cables 10 to camera 5 and flash units 7, 7A to operate them when trigger 9A is activated.

Frame 2 includes a plastic channel 11 along its lower end for vertically supporting a thermographic plate 3 behind and centered within the frame so that the thermographic plate 3 is substantially free on all but its bottom edge. Frame 2 may have its upper edge 13 formed of a magnetic material to permit magnetic name plates or labels 12 to be supported thereon. Plates 14 may be disposed between and secured to the frame 2 and the crossbar 6, or the mounting bar 8, respectively in any convenient manner to form binlike holding sections 14 for film or the like. The outer sides of plates 14 may have rails 14A secured thereto.

Flash unit 7A is advantageously designed so that it is fired, for example through a photocell, when flash unit 7 is triggered.

Camera 5 may be any efficient camera desired, such as, for example, an instant-picture camera or a reflex camera. Preferably camera 5 is a commercial autofocusing camera.

In a preferred embodiment, the rails or bars 1, 1A, 6 and 8, and the camera mount 4 are all made of aluminum or optionally of a suitable plastic. The rails or bars advantageously are of square cross section. The appropriate dimensions for the apparatus are: length of rails 1 and 1A, about 48 cm; length of crossbar 6, about 53 cm; external spacing of rails 1 and 1A, about 11 cm with an internal spacing of about 7 cm; and spacing of crossbar 6 from the ends of the rails 1 and 1a, about 7 cm.

A screw 15 with a knurled knob is advantageously disposed on the rail 5A below the camera 5 for the fine longitudinal adjustment of the latter in the conventional manner for camera mounts.

As seen in FIGS. 1 and 2, the flash units 7, 7A are mounted on the cross bar 6 adjacent the frame 2 and with their light sources facing each other in positions parallel to the frame. In addition, as seen more particularly in FIG. 1, the camera mounted 4 for camera 5 supports the camera with its lens located substantially in alignment with the center of the frame and with the front of the lens generally parallel to the frame 2.

As mentioned, the apparatus is advantageously provided with a small, magnetically adhering labeling plate 16, which is secured to the upper edge 13 of the frame 2 and thus permits at all times clear identification of the thermograms. Moreover, small, magnetically adhering symbol plates 17 standing, for example, for RIGHT BREAST, LEFT BREAST, AFTER COOLING WITH AIR BLOWER, etc., are provided. These are also fastened to the upper edge 13 during the exposure and after use are kept in bins 14. These may also be formed of a magnetic material for adhesion. The magnetic labeling plates 16 and the symbol plates 17 permit rapid and clear identification of the photographically recorded thermographic findings.

The compact apparatus in accordance with the present invention lends itself to one-hand operation in the photographic recording of breast thermography. It permits thermographic plate 3 to be held near the breasts without a troublesome frame or metal parts that might come into contact with the skin. Further, through the arrangement illustrated in FIGS. 1, and 2 optimum optical relationships are obtained with respect to camera 5, flash units 7 and 7A, and thermograhic plate 3. The image area can be adjusted with respect to height by the adjustable mounting of the camera on rail 5A.

Although an illustrative embodiment of the invention has been described herein, it is to be understood that various changes and modifications may be effected, therein by those skilled in the art without departing from the scope or spirit of this invention.

What is claimed is:

1. A compact apparatus of light-weight construction for the performance and simultaneous photographic recording of plate thermography, comprising a pair of spaced generally parallel straight rails having pairs of opposed free ends; a frame mounted on and at right angles to one of said pairs of free ends and including means for holding a thermographic plate thereon, a camera mount secured to the other pair of said opposed free ends for supporting a camera thereon with the camera lens located substantially in alignment with the center of said frame and with the front of the lens parallel thereto, said mount interconnecting the two rails; said means for holding a thermographic plate being formed of plastic and located on the side of said frame away from the camera; at least one cross bar secured and extending transversely to the rails at said one end of said pairs of free ends; a pair of photographic flash units mounted in fixed spaced relation on said cross bar adjacent said frame and facing each other parallel to said frame; a camera grip; means for mounting said grip obliquely at the approximate center of gravity of the compact apparatus between said two rails; and cable means connected to said grip for tripping said flash units and a camera.

2. A compact apparatus as defined in claim 1 wherein said means on the frame for holding a thermographic plate comprises a plastic channel located only along the bottom edge of the frame for vertically mounting the thermographic plate adjacent the frame.

3. A compact apparatus as defined in claim 2 wherein said frame has magnetic adhesion means at least along its upper edge only on the side facing the camera.

4. A compact apparatus as defined in claim 3 including bin means disposed between the frame and the crossbar.

5. A compact apparatus as defined in claim 4 wherein one of said flash units includes a photocell for firing the unit when the other flash unit is triggered.

6. A compact apparatus as defined in claim 4 including an instant-picture camera mounted in said mount.

* * * * *